US 6,682,552 B2
Jan. 27, 2004

(12) United States Patent
Ramsden et al.

(54) BRAIN COOLING DEVICE AND MONITORING SYSTEM

(76) Inventors: Vivian R. Ramsden, 409 Waterloo Crescent, Saskatoon, Sasktchewan (CA), S7H 4L3; Jim Thornhill, 2336 Munroe Avenue South, Saskatoon, Saskatchewan (CA), SJ7 1S5; Tim F Hillier, Box 34, Suite 407, RR4, Saskatoon, Saskatchewan (CA), S7K 3Z7; Dale Corbett, 14 Bryon, St. John's, Newfoundland (CA), A1B 3B7; R. David Fletcher, #117 16350 White Rock, British Columbia (CA), V4A 8J8; Gill N. White, 4255 Argyle Street, Regina, Saskatchewan (CA), S4S 3M1

( * ) Notice: Subject to any disclaimer, the term of this patent is extended or adjusted under 35 U.S.C. 154(b) by 0 days.

(21) Appl. No.: 09/953,204

(22) Filed: Sep. 17, 2001

(65) Prior Publication Data
US 2003/0055473 A1 Mar. 20, 2003

(51) Int. Cl.⁷ .................................................. A61F 7/00
(52) U.S. Cl. ........................................ 607/109; 607/114
(58) Field of Search ........................ 607/108, 109, 607/114, 112, 96; 606/20, 27

(56) References Cited

U.S. PATENT DOCUMENTS

| | | | | |
|---|---|---|---|---|
| 1,610,712 A | * | 12/1926 | Schweinert | 607/109 |
| 2,250,840 A | * | 7/1941 | Pomeranz | 607/109 |
| 4,566,455 A | | 1/1986 | Kramer | |
| 4,576,169 A | * | 3/1986 | Williams | 607/109 |
| 4,750,493 A | | 6/1988 | Brader | |
| 4,783,866 A | | 11/1988 | Simmons et al. | |
| 4,832,030 A | * | 5/1989 | De Canto | 607/109 |
| 4,920,963 A | | 5/1990 | Brader | |
| 5,005,374 A | * | 4/1991 | Spitler | 62/259.3 |
| 5,190,032 A | | 3/1993 | Zacoi | |
| 5,400,617 A | * | 3/1995 | Ragonesi et al. | 62/530 |
| 5,486,204 A | | 1/1996 | Clifton | |
| 5,643,336 A | | 7/1997 | Lopez-Claros | |
| 5,861,022 A | * | 1/1999 | Hipskind | 607/109 |
| 5,871,526 A | * | 2/1999 | Gibbs et al. | 607/104 |
| 5,897,581 A | | 4/1999 | Fronda et al. | |
| 5,913,885 A | | 6/1999 | Klatz et al. | |
| 5,916,242 A | | 6/1999 | Schwartz | |
| 5,957,964 A | | 9/1999 | Ceravolo | |
| 5,980,561 A | * | 11/1999 | Kolen et al. | 607/104 |
| 6,030,412 A | | 2/2000 | Klatz et al. | |
| 6,416,532 B1 | * | 7/2002 | Fallik | 607/109 |
| 2002/0120317 A1 | * | 8/2002 | Fletcher | 607/109 |

FOREIGN PATENT DOCUMENTS

| | | |
|---|---|---|
| JP | 09-072152 | 10/1998 |
| JP | 10-250455 | 2/2000 |
| WO | WO 9856310 | 12/1998 |

OTHER PUBLICATIONS

Dietrich et al., "Effects of Normothermic Versus Mild Hyperthermic Forebrain Ischemia in Rats", *Stroke*, vol. 21, No. 9, Sep. 1990 pp. 1318–1325.

(List continued on next page.)

*Primary Examiner*—Rosiland K. Rollins
*Assistant Examiner*—Rosiland Stacie Kearney
(74) *Attorney, Agent, or Firm*—Kathleen E. Marsman; Borden Ladner Gervais LLP

(57) ABSTRACT

A device and system designed for use in a pre-hospital setting to cool the brain after injury is described. The device incorporates a cold insert into an arch that fits around the neck of a subject, without obstructing the airway of the subject. A cold insert, such as a frozen fluid or endothermic packet, is disposed within one or both of the terminal ends of the arch, adjacent to one or both of the subject's carotid arteries. The cooling effect is specifically directed to cool the blood flowing through the carotid artery to the brain. A system incorporating the device with a temperature monitor is also disclosed. The system allows a health care professional to monitor and regulate cooling as required in the pre-hospital setting.

15 Claims, 3 Drawing Sheets

OTHER PUBLICATIONS

Colbourne & Corbett, "Delayed and prolonged post–ischemic hypothermia is neuroprotective in the gerbil", *Brain Research*, vol. 654, May 10, 1994, pp. 265–272.

Reith et al., "Body temperature in acute stroke: relation to stroke severity, infarct size, mortality, and outcome", *The Lancet*, vol 347, Feb. 17, 1996, pp. 422–425.

Schwab et al., "Brain temperature monitoring and modulation in patients with severe MCA infarction", *Neurology 48*, Mar. 1997, pp. 762–767.

Slade et al., "Effect of Therapeutic Hypothermia on the Incidence and Treatment of Intracranial Hypertension", *J. Neuroscience Nursing*, vol. 31, No. 5, Oct. 1999, pp. 264–269.

Kammersgaard et al, "Feasibility and Safety of Inducing Modest Hypothermia in Awake Patients With Acute Stroke Through Surface Cooling: A Case–Control Study", Stroke, Sep. 2000, pp. 2251–2256.

Corbett et al., "Temperature Modulation (Hypothermic and Hyperthermic Conditions) and Its Influence on Histological and Behavioral Outcomes Following Cerebral Ischemia", *Brain Pathology*, vol. 10, 2000, pp. 145–152.

American Heart Association "Part 7: The Era of Reperfusion. Section 2: Acute Stroke" *Circulation 2000*; 102 (Suppl I), Aug. 22, 2000, pp. I–204 –I–216.

* cited by examiner

BRAIN COOLING DEVICE AND MONITORING SYSTEM

FIELD OF THE INVENTION

The present invention relates generally to the field of medical devices. More particularly, the present invention relates to a device and monitoring system for use in localized cooling of the brain.

BACKGROUND OF THE INVENTION

Temperature is an important variable in determining the amount of neural damage resulting from an ischemic attack (Dietrich et al, 1990). Clinically, temperature is now deemed a significant, independent risk factor for stroke (Reith et al, 1996), as well as a contributing risk factor to other risk factors for stroke such as hypertension, cigarette smoking, atrial fibrillation, diabetes, and transient ischemic attacks etc. Therapeutically, the implementation of mild hypothermia (34–36° C.) to stroke and head trauma patients is advocated as beneficial based on clinical studies (Kammersgaard et al, 2000; Schwab et al, 1997) and animal experiments indicating long term neural and behavioural benefits (Corbett & Thornhill, 2000; Colbourne & Corbett, 1994).

Clinically, whole body cooling of stroke patients has been tested with forced air cooling with the Bair Hugger Wrap and anesthesics (Kammersgaard et al, 2000) or with cooling from fans and alcohol washes (Schwab et al, 1997). Pethidine anesthestic is given to prevent shivering activation. These whole body-cooling techniques are generally effective in reducing core temperature but long term stroke outcome analysis is not yet known. More regionalized head cooling of head trauma and stroke patients has been attempted. Cooling helmets (previously cooled or having cooled water or air circulating through them) attempt to decrease brain temperature via conductive changes through the skull (Klatz & Goldman, 1995 in U.S. Pat. No. 5,913,885; Gunn & Gunn 1998 in PCT Patent Application WO98/56310). Cooling pillows for the head and neck region have also been devised to decrease the body temperature of the patient (Tsutomu & Koji, 1998 in Japanese Patent Publication 09-072152; Katsumitsu & Shinichi, 2000 in Japanese Patent Publication 10-250455). These extracranial cooling devices may take some time to internally cool the brain via convective (air) or conductive processes. Another approach (Schwartz, 1997) is to cool the brain directly via cooling the carotid arterial blood by way of a water perfused neck collar, or alternatively, cooling the oral cavity by way of a water perfused endotracheal tube.

It is important to decrease the brain temperature of suspected stroke and head trauma patients from a more internal source (eg. carotid arterial blood flowing to the brain) without unnecessarily cooling the whole patient, which will increase the chance of activating shivering mechanisms. Shivering increases body temperature, which is detrimental to the patient. In the pre-hospital setting, it would be beneficial if precise control of the magnitude a duration of the cold temperature being applied to the carotid region bilaterally could be monitored and documented. However, this is not current practice.

A number of publications relating to cooling the brain have clearly established that cooling the brain reduces damage after stroke or other head injury. Exemplary publications include Slade et al., 1999; and Corbett et al. 2000.

A variety of prior art devices have attempted to cool the head or portions thereof to avoid injury after trauma. Patents relating to such devices are discussed briefly below.

Chilling a subject's head to cool the brain is an approach disclosed in a number of patent documents. U.S. Pat. No. 5,913,885 discloses a device and method for cooling the whole head. The device includes a helmet and a neck-supporting back plate. The helmet receives a chilled fluid from an external source, or is fully surrounded with inserts capable of endothermic reactivity. U.S. Pat. No. 5,957,964 discloses a cap with a plurality of pockets for receiving pre-filled pouches of coolant, such as ice. This device is used to cool the surface of the head adjacent the cap. U.S. Pat. No. 6,030,412 discloses a hood for covering the head, neck and upper back of a patient. A coolant source is either perfused through the hood, or a combination of endothermic reactants is provided in cavities of the hood. A chin-strap can be placed in the neck area for securing the hood to a subject's head. U.S. Pat. No. 4,750,493 teaches a method of cooling the face, particulary the region adjacent the mandible. Topical cold packs are applied, incorporating ammonium nitrate pellets stored near a reservoir of water which can be combined to cause an endothermic reaction. U.S. Pat. No. 4,920,963 discloses a shroud for cooling the extracranial area of the head, including the face and mandible. The shroud contains exothermic reactants such as ammonium nitrate pellets.

The prior art devices incorporating cooling inserts generally suffer from the disadvantage that a large cooling insert is required. Surfaces of the head which are merely adjacent the brain are cooled, and thus much of the cooling effect from a large cooling insert provides superfluous cooling of the skin. Further, if a subject requires cooling over an extended period of time, replacement inserts may be required. It is inconvenient to maintain large replacement inserts in reverse for such situations. Cooling by conduction from the skull inward to the brain takes time.

Body cooling devises for use in conjunction with a thermostat or monitor have been disclosed. U.S. Pat. Nos. 4,566,455 and 5,897,581 disclose headwear for applying cold to the scalp. Scalp temperature is monitored, and the headwear has a temperature monitor pocket for holding sensors that are connected to a display. A chin-strap is used for fastening the headwear to the scalp, but the neck on chin area is not cooled. U.S. Pat. No. 5,486,204 teaches a method for inducing hypothermia to the head area after a head wound. Intravascular temperature is reduced in the whole body by cooling a subject with a cooling blanket set to 5° C. A subject is monitored to have a body temperature maintained 32–33° C. Whole body cooling is often accompanied by the negative effect of inducing shivering. U.S. Pat. No. 5,643,336 teaches a heating and cooling pad for treating the face and head with a fluid that is circulated through the pad, which is controlled by a thermostat.

Therapeutic devices for application to the neck are known. U.S. Pat. No. 4,783,866 discloses a therapy pillow having a cold pack that is contoured in a U-shape to provide intimate contact with the neck and generalized cooling to the neck, area. A pocket within the pillow is provided to fit a temperature retaining material such as a cold pack, which is also U-shaped. This device is bulky in the region behind a subject's neck, and would need to be removed to facilitate such procedures as intubation in the pre-hospital setting.

U.S. Pat. No. 5,916,242 (to Schwartz) discloses a collar for cooling the brain by cooling blood flowing through the carotid arteries. A liquid coolant or gaseous refrigerant is perfused through the collar, and passes by the carotid arteries. However, this apparatus does not allow monitoring of the coolant temperature. Further, the apparatus disclosed in this document is not amenable to a pre-hospital setting, as the perfusate must be circulated by mechanical means, such as a pump. The device is intended for use with subjects admitted to a tertiary care hospital setting thus portability is not required but accurate monitoring should be maintained.

Review of the prior art indicates that there is a need for a device or system that cools the brain in conjunction with temperature monitoring system so as to regulate the cooling effect. There is a need for a device, which provides monitored localized cooling to the brain in a way that minimizes shivering and whole-body hypothermia. Such a device is particularly necessary in a pre-hospital setting, such as during transport in an emergency vehicle.

Further, the prior art devices are relatively bulky and uncomfortable. In the pre-hospital setting, for example when a subject is being transported to hospital after injury, there is a need for a device that is comfortable and respectful of the subject's physical condition. In the case of injury to the brain induced by stroke, a subject may be transported to hospital over a long distance. Many such subjects are elderly and would find it uncomfortably, traumatic or even undignified to be encased in such devices as are dislosed in the prior art. Particularly, bulky helmet-like devices with circulating fluids or large cooling inserts are inappropriate for this reason. Further, the sheer size of the known devices prohibit them from becoming a standard item kept in a emergency vehicle, or in any other pre-hospital setting having a limited amount of storage space.

SUMMARY OF THE INVENTION

It is an object of the present invention to obviate or mitigate at least one disadvantage of previous devices and systems for cooling the brain after injury.

A brain cooling device is disclosed herein which is designed for use in a pre-hospital setting, such as an on-site emergency setting, in an ambulance or other emergency vehicle. A brain cooling system is also disclosed which includes a temperature sensor through which the brain cooling effect can be observed and/or regulated. Further, a method for cooling the brain using the device or system is disclosed.

According to the invention, there is provided a brain cooling device comprising an arch for placement around the neck of a subject, the arch having two terminal ends for placement adjacent the carotid arteries of a subject. The terminal ends are disposed so as not to block the airway of the subject. The device also has at least one pocket formed within either one or both terminal ends of the arch. A cold insert is removably retained within the pocket, and is capable of imparting a temperature lowering effect to the carotid artery so as to cool the brain of the subject. The device also includes a monitoring system with several sensors for placement on the body of a subject to detect surface body temperature changes indicative of brain cooling by the arch.

The invention further provides a brain cooling system comprising an arch for placement around the neck of a subject so as not to block the airway of the subject. At least one pocket is formed within the arch, the pocket being disposed adjacent to the carotid artery on one or both sides of neck on the subject. A cold insert can be removably retained within the pocket, and is capable of imparting a temperature lowering effect to the carotid artery of the subject so as to cool the blood entering the brain. The system further includes sensors for detecting surface body temperatures of the subject, with changes in the body temperature being indicative of brain cooling, and a digital display and read-out for indicating the temperature changes detected by the sensors.

The invention also provides a method of cooling the brain of a subject comprising the steps of placing the inventive device on the neck of a subject so as not to obstruct the airway of the subject, placing a cold insert in a pocket of the device, and replacing the cold insert when it is no longer imparting a cooling effect to the subject as identified by the skin sensors which are a part of the temperature monitoring system.

A further method falling within the scope of the invention is provided as method of cooling the brain of a subject comprising the steps of installing the brain cooling system of the invention on a subject. The system is installed so that the arch is on the neck of the subject in a manner that does not obstruct the airway of the subject, and one or more sensors are placed on the subject in regions of the body such as a neck, forehead or axilla. At least one cold insert is placed in a pocket of the arch and is replaced as needed when one or more sensors indicate that a cooling effect is no longer being imparted to the subject.

The inventive brain cooling device can be useful in reducing brain damage once a head or brain injury has been sustained, such as in stroke or head trauma caused by an accident. By cooling the brain to achieve either normothermia or mild hypothermia, brain damage can be minimized or reduced after such an injury. By localizing cooling to the carotid (neck) region instead of the whole head, shivering can be minimized. The invention allows quick cooling of the brain, yet because of the relatively small surface area of cold application, the invention minimizes the threat of rebound shivering, and reduces the requirement for prophylactic use of anesthetics. By monitoring the cooling to a desired temperature indicative of brain cooling, the brain damage following injury can be minimized.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Figure 1:
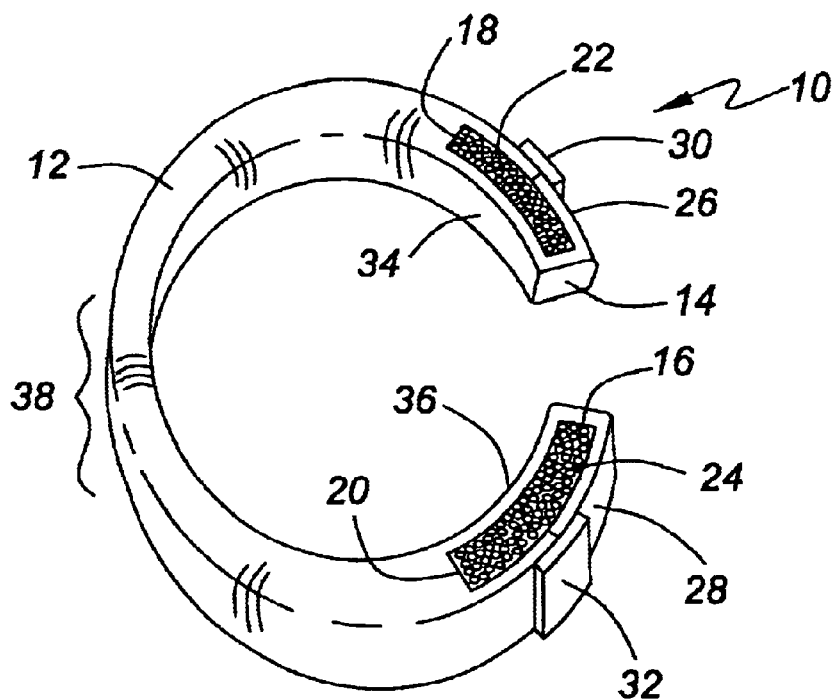
FIG. 1 illustrates an embodiment of the brain-cooling device according to the invention.

Generally, the present invention provides a device for cooling the brain following injury. The invention provides a brain-cooling device comprising an arch for placement around the neck of a subject. The arch fits around the back of the neck of a subject and has two terminal ends, which are disposed adjacent to the carotid arteries of a subject when the arch is in place. The terminal ends of the arch are disposed on either side of the throat area so as not to obstruct the airway of the subject. The device has a pocket formed within one or both of the terminal ends of the arch. A cold insert is removably retained within a pocket, and is capable of imparting a temperature lowering effect to the blood passing through the carotid artery on one or both sides so as to cool the brain of the subject. A temperature monitoring system is optionally included with the device so as to regulate the cooling effect.

The invention further relates to a brain cooling system comprising an arch for placement around the neck of a subject so as not to block the airway of the subject. At least one, and preferably two pockets are formed within the arch, each pocket being disposed adjacent to a carotid artery of the subject. A cold insert can be removably retained within a pocket, and is capable of imparting a temperature lowering effect to the blood passing through the carotid artery bilaterally of the subject so as to cool the brain. The system further includes at least one sensor for detecting surface body temperature changes of the subject, the body temperature being indicative of brain cooling, and a digital display and read-out for indicating the temperature detected by the sensors. This system may additionally include an alarm for alerting the health care providers when the temperature detected by the sensor reaches a pre-set temperature, and/or a detector for detecting the temperature of the cold insert.

The invention also relates to a method of cooling the brain of a subject involving the steps of placing the invention device, particularly the arch, on the neck of a subject so as not to obstruct the airway of the subject. A cold insert is placed in each pocket of the device and is replaced periodically when it is no longer imparting cooling effect to the subject as noted by the temperature monitoring system.

The inventive method of cooling the brain of a subject will also include a monitoring step, wherein the brain cooling system of the invention is installed on a subject by placing the arch on the neck of the subject, and placing one or more sensors on the subject in the regions of the body such as the neck, chest, forehead or axilla. Again, a cold insert is inserted in each pocket and replaced as needed.

The inventive device may be used to achieve a temperature required to impart mild brain hypothermia (from 34–36° C.). Blood passing through the carotid artery on the way to the brain is cooled by proximity to the cold inserts, which imparts cooling to the brain. A temperature indicative of a brain cooling effect is either determined clinically, through gathering data, or by assessing a subject's initial temperature and observing any decrease in temperature.

The device according to the invention is not perfused, as has been attempted in prior devices, but instead provides cold inserts to cool the blood flowing through the carotid arteries on the way to the brain. The device is flexible and/or adjustable and thus it fits snugly next to the carotid region. The arch may optionally be covered in semi-conductive, non-irritating fabric to prevent sweating, and this cover may be removed and disposed of to maintain the device itself as clean and sanitary as possible for subsequent re-use in the pre-hospital care setting. The central front-facing portion of the subject's neck (airway) is left accessible when the device is installed, so as not to impede breathing. Other devices used in an emergency setting, such a stabilization collars are bulky and often obstruct the subject's airway. The arch is compact and portable and is thus ideal for use in the pre-hospital setting.

FIG. 1 illustrates a preferred embodiment of the device according to the invention. The brain cooling device (10) comprises an arch (12), which is C-shaped and has two terminal ends (14, 16) at which pockets (18, 20) are formed. Within the pockets, cold inserts (22, 24) are located, which in this embodiment contain pre-cooled Xylite beads. The pockets are accessed through an opening (26, 28) facing the external side of the arch, which is held shut with a Velcro™ closure (30, 32). The subject-facing surface (34, 36) of each pocket is formed of a relatively thin semi-conductive material so that a cooling effect from the cold inserts (22, 24) can be imparted therethrough to the carotid artery region of a subject on whom the arch is placed. This embodiment of the arch is relatively flexible in the rear portion which fits around the back of the neck when the arch is in place. This allows for easy installation and removal of the arch on a subject.

Figure 2:
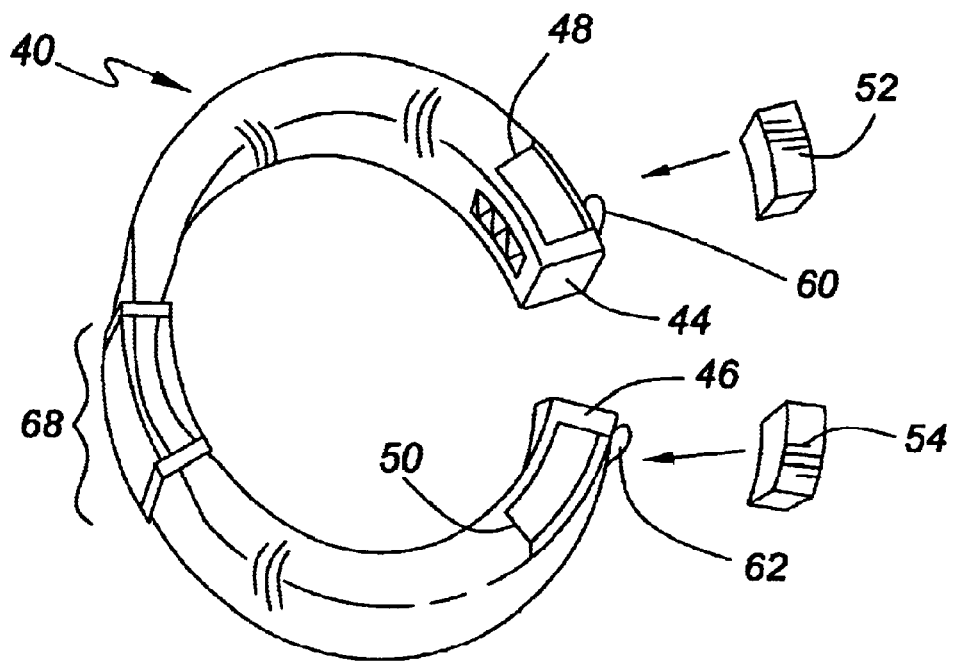
FIG. 2 illustrates a further embodiment of the device according to the invention.

FIG. 2 illustrates an alternative embodiment of the inventive brain-cooling device. The brain cooling device (40) according to this embodiment has many features in common with the device shown in FIG. 1. In this case, terminal ends (44, 46) have pockets (48, 50) formed therein. Cold inserts (52, 54) formed of encapsulated "Blue-Ice" are kept frozen prior to use and are installed into the pockets through an opening (56, 58) facing the external side of the arch at each terminal end. Each opening is held shut through the use of a loop fastener (60, 62). The subject-facing surface of the pocket comprises a nylon mesh wall (64, 66) through which a cooling effect from the cold inserts can be imparted to the subject on whom the arch is placed. The rear portion (68) of the arch is adjustable in size with a sliding adjuster that can be extended or contracted to suit the size of the subject's neck.

The Arch.

The arch is a C-shaped or U-shaped body capable of fitting around the back of a subject's neck. The arch should be comfortable, and not bulky that it impedes the appropriate body positioning of a subject being transported over a long distance in an emergency vehicle. In such situation, a subject may be on a stretcher with their head resting on a pillow. Advantageously, the arch adds minimal bulk behind the neck of the subject. When in place on a subject, the terminal ends of the arch are disposed on either side of the neck of the subject, specifically excluding coverage of the windpipe or throat area. It is undesirable to obstruct the airway of a subject, and thus advantageously, the opening of the arch corresponds to the throat area on the front-facing portion of the neck of the subject.

The arch may comprise a material capable of deformation, such as for example a plastic or polymeric material, which can be stretched open or deformed to fit onto the neck of the subject, while retaining its original shape once in place. The arch may also be formed of a more rigid material, but can be bendable or extendable so as to be telescopic. In the embodiment wherein the arch is extendable, the arch can be adjusted to different lengths or circumferences so as to be useful for various sizes of subjects.

Figure 3:
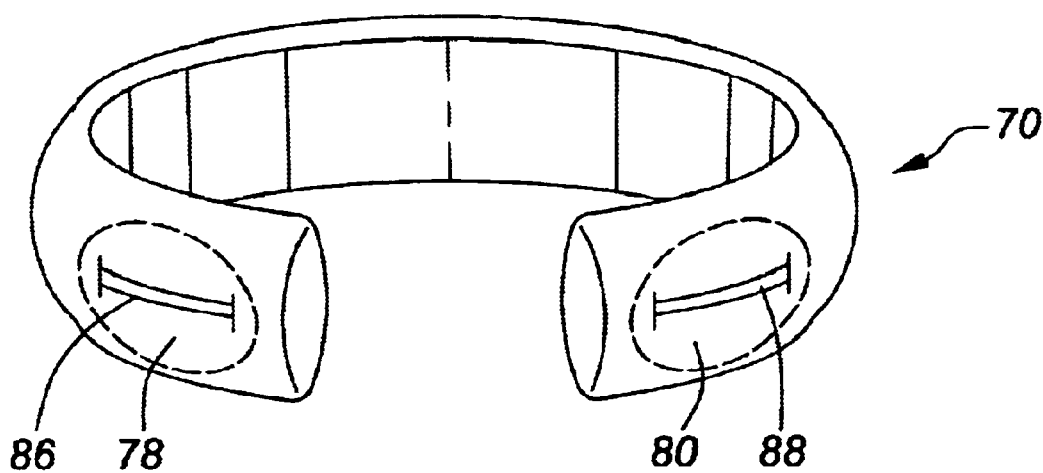
FIG. 3 illustrates an embodiment of the arch for use in the inventive device.

FIG. 3 illustrates an embodiment of an arch (70) for use in the invention. The pockets (78, 80) located at the terminal ends of the arch are suited to hold a round cold insert. A cold insert can be inserted or removed from a pocket through the slit opening (86, 88) of the pocket facing the external side of the arch.

The Removable Cover.

The inventive device may additionally comprise a removable cover encasing the arch through which said temperature lowering effect can be imparted. The removable cover may be formed of any material such as a woven or non-woven fabric, or a supple material that is soft and comfortable when placed adjacent the skin of a subject. Such a cover may be used over the arch when in place around the neck of a subject. The cover can be removed and can be disposed of once a subject has completed the use of the device. This allows re-use of the device while maintaining sanitary conditions between subjects. The removable cover may surround the entire arch or only a portion thereof. The removable cover may extend overtop of the pocket area where the cold insert is placed, provided that the material of the cover is thin enough and conductive enough to impart cooling therethrough.

The Pocket.

At least one pocket is formed at one or both terminal ends of the arch. When the arch is placed on the neck of a subject, the pocket of pockets are disposed adjacent one or both carotid arteries, respectively. The cold insert may be inserted in only one pocket of the arch. In a preferred embodiment, the arch has two pockets formed therein for retaining cold inserts, one each disposed at the a terminal end of the arch, such that when the device is in place around the neck of a subject, both carotid arteries will be adjacent to a pocket.

The pocket may be of any configuration suitable for inserting and retaining a cold insert therein. Any means of retraining the cold insert within the pocket while allowing cold to be imparted through to the subject can be used. The pocket may be round, oblong, or rectangular in shape, and should be formed so that a surface area of the cold insert can be exposed through the pocket so as to impart cooling to the subject. For example, the subject-facing portion of the pocket may comprise a mesh wall, a fabric wall that allows passage of cold therethrough, or may merely comprise an opening that allows direct exposure of a cold insert to the body surface while not allowing the cold insert to fall out. In an embodiment where the subject-facing portion of the pocket comprises a fabric wall, this well may be formed of a moisture-resistant, moisture-proof, or moisture absorbing material, so that condensation from the cold insert will not pass therethrough and drip onto the subject.

The pocket is designed so once a cold insert has warmed to ambient temperature, it can be removed from the pocket without necessitating the removal of the arch from the subject. According to an embodiment of the invention, the pocket advantageously has an opening facing an exterior side of the arch, either on the outside, top or bottom thereof. This opening allows removal and insertion of a cold insert into the pocket while the arch is in place around the neck of a subject. This opening is large enough to allow passage of a cold insert therethrough, but is configured so as to retain the cold insert within the pocket during use. In an exemplary embodiment, the cold insert is inserted and removed from the pocket through an opening facing the exterior side of the arch, which can be taken to mean any side not facing the subject when the device is in place. Alternatively, it would be possible to have the cold insert removable from the subject-facing side of the arch, and the care-giver could simply displace the terminal ends of the arch away from the subject's carotid region when replacing the cold insert. The pocket may be closable with any suitable means, such as a Velcro™ closure or an overlapping fabric closure. Further, a snap-fit cold insert could be used which is retained in the pocket by virtue of a precise shape.

The Cold Insert.

The cold insert imparts a temperature less than ambient temperature to the carotid region of the neck of the subject once the device is in place. The cold insert is retained within the pocket of the device. The cold insert comprises an encapsulated medium capable of achieving a temperature less than ambient temperature, and has an area large enough to impart such a temperature change to the carotid region so as to have a brain cooling effect. The cold insert can be kept cold in an insulted pack and changed within the pocket of the device as often as required to maintain a slightly hypothermic/normothermic temperature for the subject.

The cold insert may comprise an encapsulated medium, such as a fluid that is freezable, such as water or "Blue-Ice". Further, conductive coolable particulate, such as beads may be encapsulated within the insert. For example, non-metallic beads or seeds, or Xylite ($C_5H_{12}O_5$) can be used. Alternatively, the cold insert may contain unreacted reactants capable of an endothermic reaction. For example, these reactants may comprise unreacted pellets of ammonium nitrate ($NH_4NO_3$), which are stored adjacent to a reservoir of water, which can become intermixed as desired. A fragile membrane may be placed within the cold insert to keep the reactants apart until cooling is required, at which time a user may break the membrane while keeping the reactants intact, thereby initiating a cooling reaction as required. This embodiment is advantageous because access to a freezer is not necessary.

In use, the cold inserts comprising freezable fluid may be stored in a freezer, and when required, such as for an emergency call via ambulance, may be removed from the freezer and relocated to an insulated bag for use as required with the device. For the embodiment in which the cold inserts are unreacted reactants, the inserts may be stored within the emergency vehicle nearby the arch, and no cold storage is required.

Figure 4:
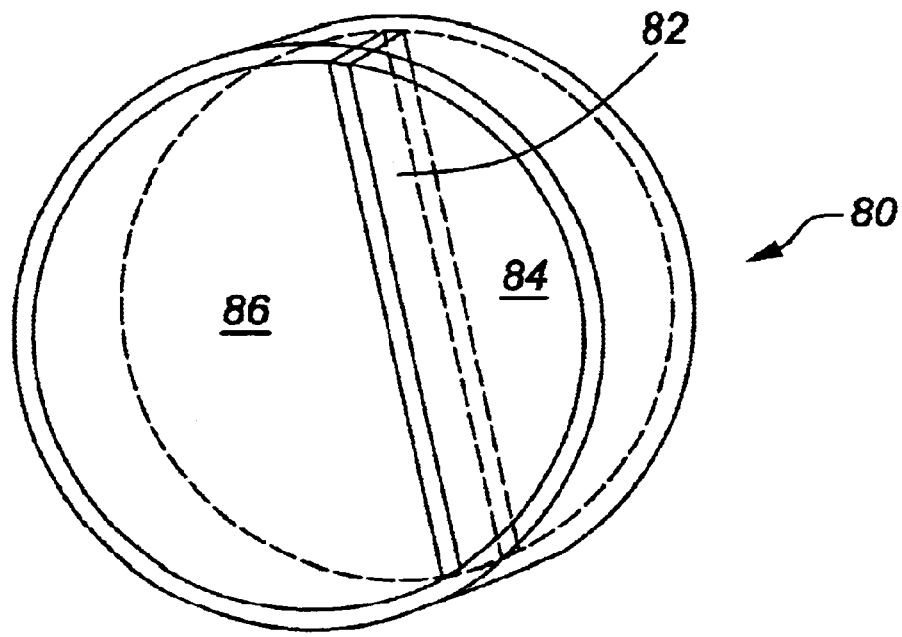
FIG. 4 illustrates an embodiment of the cold insert for use in the inventive device.

FIG. 4 illustrates an embodiment of the cold insert (80) for use in the inventive device. The insert comprises two compartments separated by a fragile membrane (82). The compartments each contain unreacted reactants which, when combined, result in an endothermic reaction. The reactant in the first compartment (84) is pellets of ammonium nitrate ($NH_4NO_3$), while the reactant in the second compartment (86) is water. When these reactants combine, a cooling effect is realized. A cold insert of the configuration can be inserted into a pocket of an arch such as shown in FIG. 3.

The Monitor.

Temperature is an extremely important vital sign and an independent risk factor in the neural and behavioural outcomes of patient experiencing a cerebral ischemic event. Yet, in the pre-hospital setting, accurate, repeated, reliable temperatures are rarely if ever monitored in these patients. An optional embodiment of the invention includes a monitor. The device including the monitor accurately and non-invasively records a regional skin temperature in one or more areas such as the neck (bilaterally), forehead and axilla of a subject, and may additionally monitor the surrounding ambient temperature. The monitor is advantageously used in conjunction with the brain cooling efforts so that localized or regionalized changes in the temperature at the one or more body surface sites can be monitored over time.

When the device is used over extended periods of time in a pre-hospital setting, such as in an emergency transport vehicle, the status of the subject can be monitored so that further action can be taken if required. Once an advantageous level of brain cooling has been accomplished, as determined by reaching a pre-determined temperature indicative of brain cooling, the cooling efforts can be reduced. Alternatively, by monitoring the temperature of a subject, if increased efforts are needed to accomplish the desired level of brain cooling, the inserts could be replaced or an alternative strategy for cooling could be devised.

The cold inserts can only impart cold to the carotid area while there is adequate differential between the ambient temperature and the temperature of the cold insert. The monitor may be used not only to monitor be temperature of the subject, but can also be used to monitor temperature of the cold insert itself.

The monitor comprises a sensor for placement on the body of a subject so as to detect a body temperature indicative of brain cooling. For example, placement of the sensor may be on a region of the body selected from the group consisting of the neck chest, temple, forehead and axilla. For example, one or more forehead (temporal) sensors may be applied, a sensor in the chest area, carotid area (away from the cold inserts), the axilla region may have one or more sensors. Surface temperature it preferably taken so that the subject remains relatively comfortable over the duration of use of the device. Prior art use of rectal or oral temperature monitoring has the disadvantage that the subject is inconvenienced and is probably unwilling and potentially unable to allow constant monitoring of temperature in such an invasive manner.

One or more of the surface temperatures can be detected by a sensor. The sensor may be any one capable of detecting temperature, preferably by non-invasive means. The sensor preferably does not contain mercury. According to a preferred embodiment, the sensor my comprise one or more thermistor probes maintained on the subject through an adhesive disc or tape. These thermistor probes advantageously may be applied to the body surface without causing discomfort to the subject.

The monitor may additionally comprise a display to indicate the temperature detected by the sensor. For example, a telethermometer can be used which is associated with the thermistor probes. The telethermometer may be multi-channelled and thus capable of displaying a plurality of temperatures from respective sensors placed on the body of the subject.

The monitor may additionally comprise an alarm that alerts when the temperature detected by the sensor reaches a pre-set temperature. This could be, for example, incorporated into the telethermometer. By alerting the user, such as the emergency health care provider, to the temperature lowering, the user can then either reduce the rate of cooling, or increase the rate of cooling as needed. The pre-set temperature can be one determined by those skilled in the art with minimal experimentation. For example, to achieve moderate brain cooling, the average body surface temperature associate with moderate cooling is recorded within the alarm function of the monitor. Alternatively, the subject's initial temperature is used as a control temperature, and the alarm can be pre-set to alert when the initial surface temperature of the subject is reduced by an adequate amount of for example, 1 to 3 degrees. Further, as the cooling is monitor it can be observed if a subject's temperature has reached a plateau, or is rising. This change is detected by the monitor and an alert could sound to advise that the cold insert requires replacement. Optionally, alarm lights or sound can be activated if threshold pre-set temperatures are met or surpassed.

The monitor may additionally comprise a detector for detecting the temperature of the cold insert itself. In this way, when the cold insert has imparted most of its cooling effect to the subject, and is rising to equilibrated with ambient temperature, the health care provider can become aware of this and can easily replace the cold insert. This may be particularly advantageous over longer periods of transport to a health care facility during which more than one insert may be required to achieve optimal brain cooling.

According to an embodiment of the invention, the monitor comprises a digital tele-thermometer, an ambient (vehicle/room) temperature probe, and skin surface temperature probes for axilla, forehead, and neck (bilateral probes). The temperature sensors report to a multi-channel thermometer. Threshold temperatures are maintained, and a display or output of temperature readings is provided The telethermometer may be powered by re-chargeable batteries, or by AC power.

Figure 5:
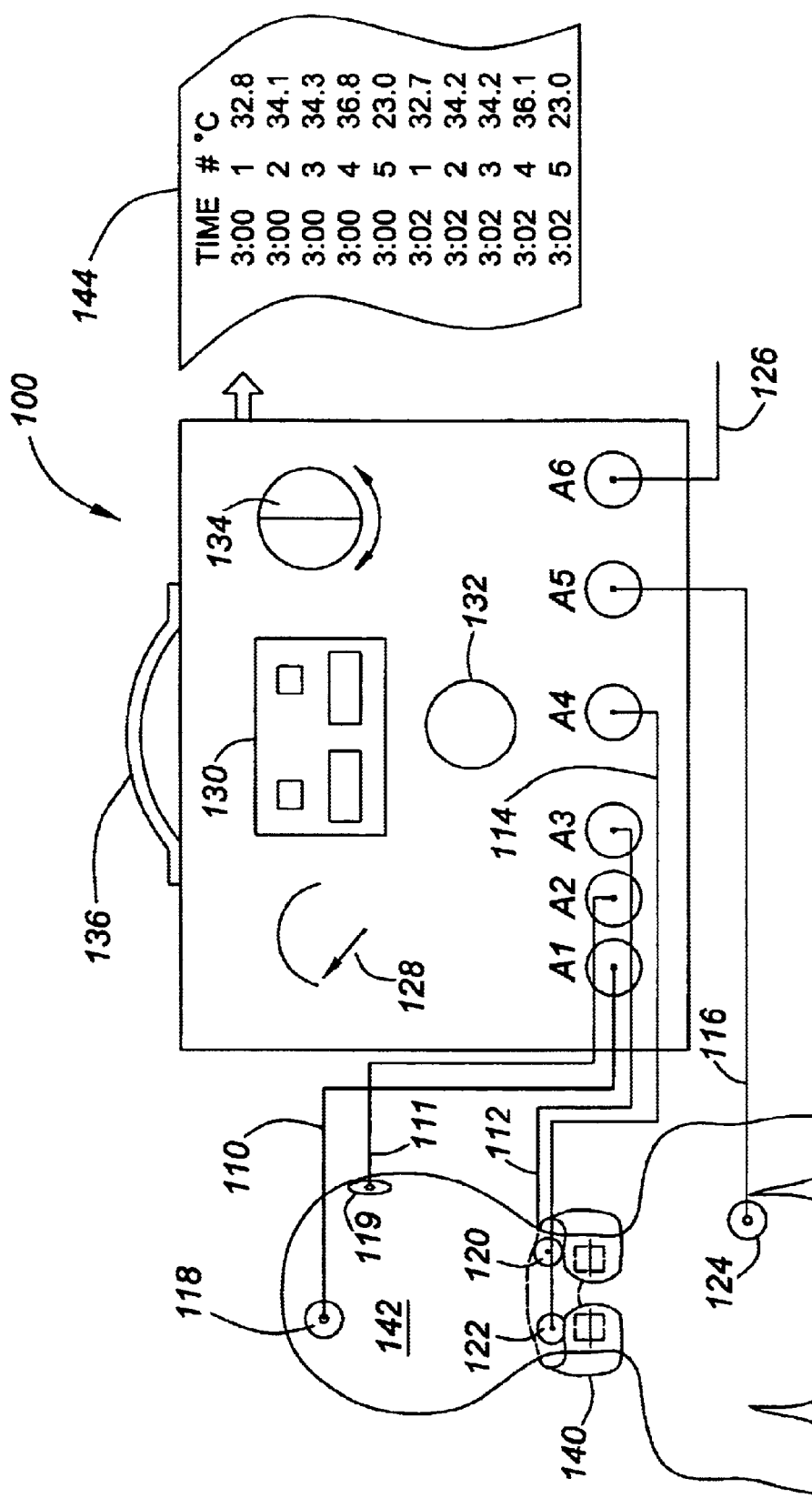
FIG. 5 illustrates an embodiment of the invention incorporating a multi-channel digital telethermometer.

FIG. 5 is a schematic overview of an embodiment of the device, including a monitor (100), according to the invention. In this case, the monitor (100) comprises a multi-channel digital telethermometer. The telethermometer has 6 channels (A1 to A6). Channels A1 to A5 are sensors which read the temperature from a thermistor probe (110, 111, 112, 114, 116) attached to the subject with an adhesive disk (118, 119, 120, 122, 124) to different surfaces of the body. Channel A1 reads from the forehead, channel A2 reads from the temple, channels A3 and A4 read from respective sides of the neck, and channel A5 reads from the axilla region. A fifth thermistor probe (126) reads the ambient air temperature on channel A6. A function dial (128) allows changes in the monitor readings, for example from auto to manual, and LED display (130) allows display of readings from various channels, a red LED is provided as an alarm (132). Should one of the channels meet or surpass a pre-set temperature, the alarm can light up to alert the health care provider of this temperature. Calibration of the monitor can be accomplished using the calibration dial (134). The monitor (100) is portable, and can be carried by a handle (136).

In use, the arch (140) having cold inserts disposed therein is placed on the neck of a subject (142) so that a cooling effect is imparted in the region of the carotid arteries. The thermistor probes (110, 111, 112, 114, 116) are attached to the subject with adhesive disks (118, 119, 120, 122, 124). Readings of temperature are taken by the monitor (100), including a reading of the ambient air temperature by probe (126). Readings from the monitor are transferred to a memory or to a printer output (144) for future use. When one or more temperatures read by the thermistor probes reaches a pre-set value, the alarm (132) may alert the health care provider that the temperature of the subject requires attention. If the temperature of the subject is rising, indicative that a brain cooling effect is no longer being imparted by the cold inserts, the alarm alerts the health care provider to replace the cold inserts within the arch (140), if for example, the insert has equilibrated to ambient room temperature.

Cooling Device for Pre-Hospital Setting.

Mild hypothermia has been recently shown in the clinical setting and, previously, from animal studies to be an effective strategy for neuroprotection from the neural damage resulting from cerebral ischemia. However, the introduction of cooling techniques has not been implemented in the pre-hospital setting (home, ambulance) for patients with suspected stroke/cerebral ischemic, or TIA (transient ischemic attack). The invention provides a portable, simple, brain-cooling device which fits comfortably around the neck of suspected ischemic subjects, yet is located firmly adjacent to the carotid region on both sides of the neck. Cold inserts are placed into one or both terminal ends of the arch so as to cool the carotid blood as it passes by on its way to the brain. In is way, brain temperature is quickly decreased, yet rebound shivering mechanisms are not activated, thus, the use of anesthetics to inhibit shivering can be avoided in these ischemic patients.

Since temperature is a critical determinant toward stroke outcome, it is imperative that the health care system has available effective and reliable devices and protocols to monitor and, if need be, facilitate intervention of the core temperature of suspected stroke/ischemic patients in the pre-hospital setting. Knowing that the therapeutic window for intervention is relatively small (3–6 hours post event), and that mild hypothermia/normothermia strategies have the capability of extending that window, it is important that health care providers have accurate data from the determination of temperature in suspected stroke/ischemic patients, as well as, the ability to safely and effectively alter the core temperature in these patients, if need be. According to an embodiment of the invention, a monitor is included that accurately and simply monitors and documents neck (bilaterally), axilla, temple, chest, and/or forehead temperatures in a suspected stroke/ischemic subject in the pre-hospital setting without any need for change in equipment upon arrival to the Emergency Department. A regionalized mild hypothermia/normothermia can be achieved according to the invention to cool the blood on the way to the brain.

In the embodiments, which include a monitor, the device can implement mild hypothermia. The return to normothermia can be continuously monitored by a health care provider. With this system, the subject can be continuous monitored for temperature from home to the Emergency Department, and mild hypothermia can be induced as required. Monitoring provides a baseline temperature determination, which is recommended. Even a drop of 1° C. in brain temperature would provide protection for the brain after trauma. The effectiveness and long-term outcome of cold therapy intervention in the pre-hospital care setting with subjects that present with a stroke or head trauma is not fully elucidated, and the inventive device including the monitor would begin to build new knowledge. The monitor allows temperature feedback that could quickly dictate the intensity and duration of the cold therapy. The device can be utilized for many other types of subjects in the pre-hospital setting that are thought to have temperature related disorders, which could benefit from brain cooling.

In considering the intervention known as cold therapy, it is believed that this therapeutic intervention should be established as soon as possible in an individual that has had either a stroke or sustained any type of head trauma. To facilitate early invention either at the scene or on the way to the hospital, portability of the brain cooling device, and optionally, the accurate monitoring of the effects of this therapeutic intervention, are important. Although the application of cold therapy is important, the ability to monitor the effect of cold therapy on the body temperature of the individual is also important. Monitoring has not been emphasized as an important aspect of conventional devices directed at carotid artery cooling as devised for either the pre-hospital or hospital settings. Monitoring allows evaluation of a subject's temperature for a feedback, loop. Monitoring also allows evaluation of how much or how little the applied cold has effected the temperature of the subject so that adjustments can be made efficiently and effectively when necessary. In addition, regular determination or evaluation of the subject's temperature by the monitoring device will minimize any potential deleterious effects of decreasing core temperature.

The portability of a brain-cooling device according to the invention facilitates cold therapy in either conscious or unconscious subjects. This device comfortably fits around the neck of the subject in a variety of settings: home, in the ambulance or even in the hospital. The carotid arteries are a quick, direct way of cooling the brain it is important that cooling therapy be commenced as soon as possible.

In the current guidelines for the management of Acute Stroke (AHA, 2000), an immediate general assessment by pre-hospital care providers within ten minutes of arriving at the scene includes the assessment of vital signs which are defined as pulse, respiration, blood pressure and temperature. This baseline determination of temperature, as advocated in the above AHA guidelines, would provide the evidence required for the application of an evidence-based intervention, cold therapy, if appropriate.

It is advantageous that cold therapy begins as early as possible, and preferably in the pre-hospital setting. In the pre-hospital setting, if a baseline temperature determination is initially done then the need for cold therapy can be determined. In addition to this, provision of a continuous feedback loop facilitates quality assurance regarding the effect that cold therapy is having on a subject and in turn minimize any possible deleterious effects of hypothermia.

The monitor according to an embodiment of the invention is non-invasive, as the determination of the surface temperatures of the body are the only ones being determined, which allows health care providers to easily take these temperatures as often as required to ensure optimal management of the subject.

The monitor enhances communication between the care provider in the pre-hospital setting and the care providers in the Emergency Department. This will help facilitate a seamless transfer of the subject to the Emergency Department, a very important criteria for optimal management of the subject.

The above-described embodiments of the present invention are intended to be examples only. Alterations, modifications and variations may be effected to the particular embodiments by those of skill in the art without departing from the scope of the invention, which is defined solely by the claims appended hereto.

References

American Heart Association (2000). Part 7: The era of reperfusion—Section 2: Acute stroke. *Circulation,* 102 (suppl I), I-204–I-216.

Colbourne F & Corbett D (1994). Delayed and prolonged post-ischemic hypothermia is neuroprotective in the gerbil. *Brain Research,* 654, 265–272.

Corbett D & Thornhill J (2000). Temperature modulation (hypothermic and hyperthermic conditions) and its influence on histological and behavioural outcomes following cerebral ischemia. *Brain Pathology,* 10, 145–152.

Dietrich W D, Busto R, Valdes I & Loor Y (1990). Effects of normothermic versus mild hyperthermic forebrain ischemia in rats. *Stroke,* 21, 1318–1325.

Kammersgaard L P, Rasmussen B H, Jørgensen H S, Reith J, Weber U, Olsen T S (2000). Feasibilty and safety of inducing modest hypothermia in awake patients with acute stroke through surface cooling: A case-control study (The Copenhagen Stroke Study). *Stroke* 31, 2251–2256.

Reith J, Jørgensen S, Pedersen P M, Nakayama H, Raaschou H O, Jeppesen L L, Olsen T S (1996). Body temperature in acute stroke relation to stroke severity, infarct size, mortality, and outcome. *Lancet,* 347, 422–425.

Schwab S, Spranger M, Aschoff A, Steiner T & Hacke W (1997). Brain temperature monitoring and modulation in patients with severe MCA infarction. *Neurology,* 48, 762–767.

Slade J, Kerr M E & Marion D (1999). Effect of therapeutic hypothermia on the incidence and treatment of intracranial hypertension. *J Neuroscience Nursing,* 31(5), 264–269.

We claim:

1. A brain cooling device comprising:
   a C-shaped arch for placement around the neck of a subject, the arch having two terminal ends for placement adjacent the carotid arteries of a subject, the terminal ends being disposed apart from each other and not connected to each other so as not to block the airway of the subject when in place around the neck of a subject, the arch comprising a material capable of deformation;
   a pocket formed within each of the two terminal ends of said arch; and
   a cold insert removably retained within each pocket and being capable of imparting a temperature lowering effect to the carotid artery so as to cool the brain of the subject, said cold insert comprising an encapsulated medium capable of achieving a temperature less than ambient temperature.

2. The device of claim 1 wherein the encapsulated medium is selected from the group consisting of a freezable fluid, coolable particulate, and reactants capable of an endothermic reaction.

3. The device of claim 1 additionally comprising a removable cover encasing the arch through which said temperature lowering effect is imparted.

4. The device of claim 1 wherein the pocket comprises an opening facing an exterior side of the arch.

5. The device of claim 4 wherein the cold insert is removable from the pocket through the opening facing the exterior side of the arch.

6. The device of claim 1 additionally comprising a monitor having a sensor for placement on the body of a subject, in a region other than the brain, to detect a body temperature indicative of brain cooling.

7. The device according to claim 6 wherein the sensor is placed on a region of the body selected from the group consisting of the neck, chest, forehead and axilla.

8. The device of claim 6 wherein the monitor additionally comprises a display to indicate the temperature detected by the sensor.

9. The device of claim 6 wherein the monitor additionally comprises an alarm that alerts when the temperature detected by the sensor reaches a pre-set temperature.

10. The device of claim 6 wherein the monitor additionally comprises a detector for detecting the temperature of at least one cold insert.

11. A method of cooling the brain of a subject comprising the steps of:
    placing the device of claim 1 on the neck of a subject so as not to obstruct the airway of the subject;
    placing a cold insert into each pocket; and
    replacing each cold insert when it is no longer imparting a cooling effect to the subject.

12. A brain cooling system comprising:
    a C-shaped arch for placement around the neck of a subject, the arch having two terminal ends for placement adjacent the carotid arteries of a subject, the terminal ends being disposed apart from each other and not connected to each other so as not to block the airway of the subject when in place around the neck of a subject, the arch comprising a material capable of deformation;
    a pocket formed within each of the two terminal ends of the arch, each pocket being disposed adjacent a carotid artery of the subject;
    a cold insert removably retained within each pocket and being capable of imparting a temperature lowering effect to the carotid artery of the subject so as to cool the brain, said cold insert comprising an encapsulated medium capable of achieving a temperature less than ambient temperature; and
    a sensor for detecting a body temperature of the subject in a region other than the brain, the body temperature being indicative of brain cooling; and
    a display for indicating the temperature detected by the sensor.

13. The system of claim 12 additionally comprising an alarm for alerting when the temperature detected by the sensor reaches a pre-set temperature.

14. The system of claim 12 additionally comprising a detector for detecting the temperature of at least one cold insert.

15. A method of cooling the brain of a subject comprising the steps of:
    installing the brain cooling system of claim 12 on a subject so that the arch is on the neck of the subject so as not to obstruct the airway of the subject, and the sensor is placed on the subject in a region selected from the group consisting of the neck, forehead and axilla;
    placing a cold insert in the pocket; and
    replacing each cold insert when the sensor indicates that a brain cooling effect is no longer being imparted to the subject.

* * * * *